United States Patent [19]
Garrett

[11] 4,229,796
[45] Oct. 21, 1980

[54] PROGRAMMED CONTROLLER FOR ULTRASONIC TESTING

[75] Inventor: Steven H. Garrett, Charlotte, N.C.

[73] Assignee: Westinghouse Electric Corp., Pittsburgh, Pa.

[21] Appl. No.: 12,543

[22] Filed: Feb. 15, 1979

[51] Int. Cl.³ .............................................. G01N 29/04
[52] U.S. Cl. .................................. 364/507; 364/506; 364/580; 73/622; 73/634
[58] Field of Search .................. 364/507, 580, 506; 73/620, 622, 623, 634

[56] References Cited

U.S. PATENT DOCUMENTS

| | | | |
|---|---|---|---|
| 3,857,052 | 12/1974 | Beller | 73/620 |
| 3,896,662 | 7/1975 | Camp et al. | 73/622 |
| 3,958,451 | 5/1976 | Richardson | 73/622 |
| 3,960,006 | 6/1976 | Smith | 73/622 |
| 4,114,456 | 9/1978 | Dory | 73/622 |

OTHER PUBLICATIONS

Material Eval. vol. 21, No. 10–Expanding The Capability of a Laboratory Ultrasonic Testing Facility By Moyer & Gray, Published in Oct. 1973 pp. 193-204.
Ultrasonics–Donar: A Computer Processing System to Extend Ultrasonic Pulse-Echo Testing By Lees et al., Published in Jul. 1973 pp. 165-173.

*Primary Examiner*—Charles E. Atkinson
*Assistant Examiner*—Gary Chin
*Attorney, Agent, or Firm*—W. E. Zitelli

[57] ABSTRACT

A system for ultrasonically testing the material of a turbine rotor includes a drive unit for axially indexing and angularly orienting a plurality of crystal transducers through the bore of the turbine rotor under test; an ultrasonic tester for electronically activating the crystal transducers as they are indexed through the rotor bore to transmit ultrasonic signals which are propagated through the rotor material and for receiving the back reflected echo signals corresponding to the ultrasonic transmissions; and a programmed electronic controller electrically interfaced to the drive unit and ultrasonic tester for adaptively coordinating the operation thereof in a selected one of a plurality of control modes to observe generated anomaly indications and measured test data parameters from the drive unit and ultrasonic tester which are used to determine the size and location of a detected potential imperfection in the rotor material and to adaptively control the drive unit in accordance with a function based on the anomaly indications and observed measured parameters of the drive unit and ultrasonic tester. Accordingly, prespecified portions of the observed measured parameters are automatically recorded, at times, during the ultrasonic testing operations to provide information relating to the size and location of the potential imperfections.

9 Claims, 11 Drawing Figures

PROGRAMMED CONTROLLER FOR ULTRASONIC TESTING

BACKGROUND OF THE INVENTION

The present invention relates broadly to the field of ultrasonically testing of turbine rotors and more particularly, to a programmed microprocessor-based electronic controller for adaptively coordinating the ultrasonic testing operations of an ultrasonic tester and associated drive unit in a selected one of a plurality of control modes, each control mode conducted in accordance with observable test data and anomaly indications generated from the ultrasonic tester and drive unit during testing operations.

Ultrasonic testing of turbine rotor shafts is primarily performed as a form of preventive maintenance to uncover imperfections in the rotor material such as slight fractures, differences in crystalline structure and even small inclusions from a piece of slag or some other nonhomogeneous matter, for example, that is, anything which may reflect propagated ultrasonic waves differently from within the rotor material. Normally, these types of imperfections are not visible upon inspection of a turbine rotor under test. Ultrasonic testing of the turbine rotors may be conducted after construction at the assembly plant and during planned shutdown maintenance intervals for a turbine system at a user's facility.

Generally, during an ultrasonic rotor test, one or more crystal transducers, usually attached arcuately about one end of a mechanical arm, are axially positioned and angularly oriented through the bore of a turbine rotor under test. The axial and angular positioning of the crystal transducers is generally brought about by a motor drive unit which indexes the one end of the mechanical arm through the rotor bore at predetermined increments, say one-fourth inch, for example, while simultaneously rotating the crystals about the longitudinal axis of the mechanical arm in an arc of approximately 375° with each incremental movement. Working independently of the motor drive unit is an ultrasonic tester which is electrically coupled to the crystal transducers to pulse them at periodic intervals causing ultrasonic signals to be propagated into the turbine rotor material and to receive from them, the back reflected echo signals associated with each ultrasonic pulse transmission. Some ultrasonic testers are of the type which normalize and linearize the received echo signals with respect to predetermined time intervals within the reception time between transmitted ultrasonic pulses. The time delay between the pulse transmission and reception of the back reflected echo signal is representative of the radial distance or depth location within the turbine rotor material thickness which is causing the reflection and the amplitude level of the back reflected echo signal is a measure of the size of the potential imperfection. In these type testers, the conditioned amplitude level of the received echo signals may be compared to an adjustable threshold level so as to render an anomaly indication corresponding to the times when the conditioned echo signals exceed the adjusted threshold level. Normally, the conditioned reflected signals are displayed on the screen of a CRT on a trace which is usually synchronized to the ultrasonic signal transmissions and time scaled in relation to the radial dimensions of the turbine rotor material thickness.

Typically, the ultrasonic testing of turbine rotors is conducted manually by an operator who initially calibrates the motor drive unit and ultrasonic tester according to well-known calibration procedures. Once this is accomplished, the operator adjusts the motor drive unit to index the mechanical arm and crystal transducers through the rotor bore in predetermined increments and adjusts the ultrasonic tester to pulse the crystal transducers with a periodicity adequate for the range of rotor material thickness and sufficient to provide for a visible display of the conditioned echo signals on the screen of the CRT. Thereafter, the motor drive unit indexes the mechanical arm through the rotor bore until an anomaly indication is generated by the ultrasonic tester at which time the drive motor is stopped. Normally, there is a time delay between the detection of the anomaly condition and the stopping of the drive motor. Consequently, the operator must manually adjust the drive motor to maximize the amplitude level of the conditioned reflected echo signal as displayed on the screen of the CRT so as to identify the maximum amplitude and exact location of the potential imperfections in the rotor material. This adjustment is a very tedious and time consuming portion of the ultrasonic testing process.

Once the operator feels that the conditioned echo signal has been maximized, he records its amplitude level and representative depth within the rotor thickness as a function of time with respect to the synchronized ultrasonic transmission pulses. The axial positions and angular orientation of the crystal transducers within the rotor bore are also recorded in addition to the crystal transducer channel which is receiving the maximized anomaly reflection. These testing steps are repeated and testing data recorded for each anomaly condition detected by the ultrasonic tester. A complete ultrasonic test of a typical rotor assembly takes approximately 12 to 20 hours using the procedure described above. When the ultrasonic testing is performed at a user's facility, the handwritten tabulated test data is mailed to a central quality control center for evaluation. Results of the evaluation are provided by return mail.

It is evident that the present ultrasonic testing apparatus for identifying potential imperfections in turbine rotors requires the constant attention of an operator for operating the equipment and recording the locations and magnitudes of the potential imperfections resulting in anomaly indications. Consequently, at least one operator is tied up for approximately 12-20 hours of testing the turbine rotor. This results not only in a handicap and inefficiency in manpower allocation, but also renders the turbine system unavailable for other maintenance functions, thus extending the planned maintenance shutdown time. One possibility for relieving the time and labors burdens associated with the present ultrasonic testing procedures is to reduce or eliminate the necessity of the operator element during the testing phase by automating the ultrasonic testing procedures. It is felt that an electronically automated ultrasonic system will decrease testing time and free the operator for other maintenance duties, offer more accurate and better tabulated test data with regard to measuring the effective geometric locations and magnitude of the potential imperfections, and may even provide the test results in a transmittable form for telecommunications between a quality control center and the test site to decrease the delay time for receiving the evaluation results identifying the severity of the uncovered anomalies.

SUMMARY OF THE INVENTION

In a system for ultrasonically testing the material of a turbine rotor, a drive unit is operative to axially position and angularly orient at least one crystal transducer within the bore of the turbine rotor under test and an electronic ultrasonic tester is operative to activate the at least one crystal transducer to transmit ultrasonic signals into the rotor material and to receive electrical signals from the at least one crystal transducer which are representative of back reflected echo signals from the transmitted ultrasonic signals. The electronic ultrasonic tester is further operative to generate test data signals representative of measurable parameters with respect to the operation thereof, preferably including the amplitude of the received electrical signal and its corresponding back reflected echo depth within the rotor material, and to generate anomaly indications, preferably at times when the back reflected echo signals exceed a predetermined reference threshold, representative of the detection of a potential imperfection in the turbine rotor material. In addition, the drive unit is also further operative to generate test data signals representative of measurable parameters with respect to the operation thereof, preferably including the axial position and angular orientation of the at least one crystal transducer within the rotor bore.

In accordance with the present invention, a programmed microprocessor-based electronic controller is electrically interfaced with both the drive unit and ultrasonic tester for adaptively coordinating the ultrasonic testing operations performed thereby in a selected one of a plurality of control modes. More specifically, the electronic controller comprises a memory unit for storing a plurality of programmed sets of instructions and data digital words which characterize the operation of the electronic controller; a microprocessor means operative to process the plurality of programmed sets of instructions and data words stored in the memory unit; a first electrical interfacing means governed by the microprocessor means to observe the test data signals and anomaly indications generated by the ultrasonic tester; a second electrical interfacing means governed by the microprocessor means to observe the test data signals generated by the drive unit and to adaptively control the drive unit in accordance with the values of the test data signals observed from the drive unit and ultrasonic tester and at times, the generated anomaly indications; and an operator interactive device which is operative to enter instructional and initializational test information to the programmed electronic controller and to record ultrasonic test data resulting from the operations of the electronic recorder.

In another aspect of the present invention, the electronic controller is programmed to adjust the gain characterization of a receive amplifier disposed in the ultrasonic tester, preferably at times, when an observed signal representative of the output of the receiver amplifier is determined to have an amplitude which exceeds a preselected amplitude range level. Accordingly, the adjustment of the gain characterization is in a direction to bring the observed amplifier output signal back within the preselected amplitude range level. Yet another aspect of the present invention permits the programmed electronic controller to uncover within the turbine rotor material an axial dimension interval, associated with a common angular interval of crystal transducer rotation, over which an excessive number of anomaly indications are generated by the ultrasonic tester and observed by the first interfacing means. Whereupon, the drive unit is governed to reposition the at least one crystal transducer to an axial position corresponding to the approximate beginning of the observed axial dimension interval for retraversing the interval at smaller indexing increments to achieve a closer ultrasonic test inspection of the rotor material volume associated therewith. Still further, the electronic controller is programmed to derive the effective values of the size and location of the potential imperfections associated with the anomaly indications for recordation on the operator's interactive device.

DESCRIPTION OF THE PREFERRED EMBODIMENT

Figure 1:
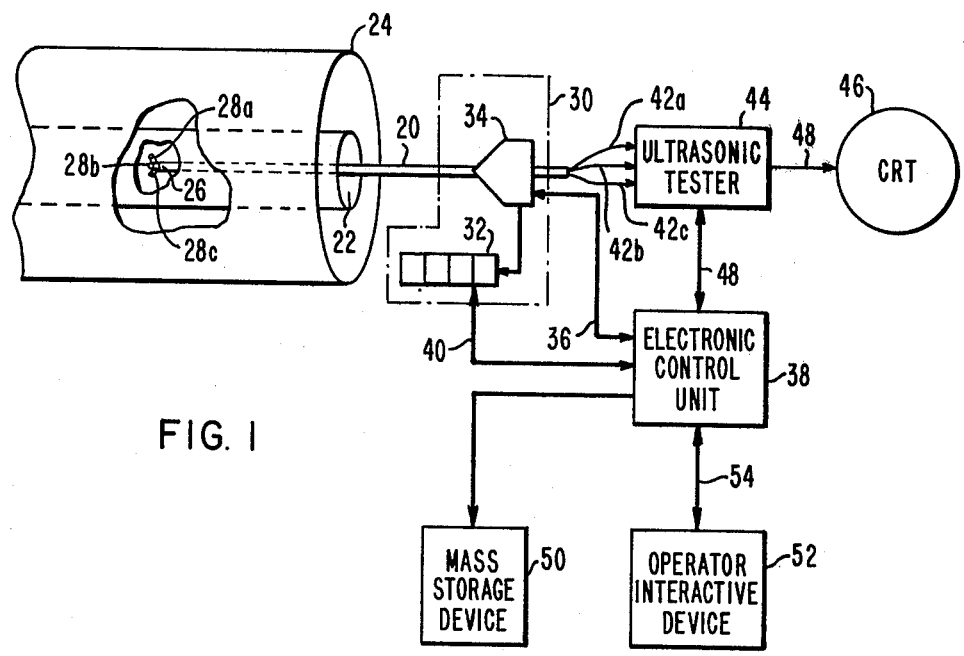
FIG. 1 is a block diagram schematic of an ultrasonic testing system suitable for embodying the principles of the present invention.

In FIG. 1 is shown a block diagram schematic of an ultrasonic testing system for identifying imperfections in a turbine rotor material suitable for embodying the present invention. Referring to FIG. 1, a mechanical arm 20 is incrementally indexed into the bore 22 of a typical turbine rotor 24. At the inserted end 26 of the mechanical arm 20, there is attached a plurality of ultrasonic crystal transducers 28a, 28b and 28c arcuately disposed about the longitudinal axis of the mechanical arm 20. The mechanical arm 20 may be axially positioned into the rotor bore 22 by a conventional motor drive unit 30 similar to the type manufactured by Applied Test Systems. In addition, for the purposes of the present embodiment, the motor drive unit 30 may be modified to include a display unit 32 which may be similar to the type manufactured by Trionics for providing a digital indication of the axial position of the crystals in the turbine rotor bore 22 and their angular orientation about the longitudinal axis of the mechanical arm 20. The unit 30 is primarily comprised of a conventional drive motor and associated gearing mechanism denoted by the block 34 which is operative to index the mechanical arm 20 at predetermined increments axially through the bore 22 of the turbine rotor 24 while simultaneously rotating the crystal transducers 28 about the longitudinal axis of the mechanical arm 20 in a circular arc of approximately 375 degrees, for example, with each indexed increment. Electrical interface control lines 36 are provided from an electronic control unit 38 to govern the axial indexing and angular orienting of the plurality of crystal transducers 28a, 28b and 28c through the turbine rotor 22. Another set of electrical signals 40 permit the electronic control unit to monitor the digital display unit 32 which contains the axial positioning and angular orientation of the crystal transducers in the turbine rotor bore 22.

Signal lines 42a, 42b, and 42c form an electrical coupling between an ultrasonic tester 44 and the crystal transducers 28a, 28b and 28c which are attached to the end 26 of the mechanical arm 20. For the purposes of the present embodiment, the ultrasonic tester 44 used is of the type manufactured by Tek Tran under the name of Immerscope II. The ultrasonic tester 44 is operative in the transmit mode to activate the plurality of crystals 28a, 28b, and 28c, for example, to propagate ultrasonic bursts of energy into the turbine rotor material 24. In the receive mode, the ultrasonic tester 44 receives electrical signals from the crystal transducers 28a, 28b, and 28c which are representative of back-reflected echoes from the propagated ultrasonic transmitted signals. The ultrasonic tester 44 may also condition the received echo signals over signal lines 42a, 42b, and 42c in a manner which will be discussed in greater detail herebelow and provide this information selectively to a cathode ray tube (CRT) device 46 over signal line 48 where it may be displayed to a test operator. In another operational aspect, the ultrasonic tester 44 is additionally operative to compare the received conditioned echo signals from the crystal transducers to an adjustable reference threshold level. At times when the conditioned echo signals exceed the adjusted reference threshold level, an anomaly indication is generated by the ultrasonic tester 44.

Another set of electrical interface signals 48 are provided between the ultrasonic tester 44 and the electronic control unit 38 for the purposes of monitoring and transferring data and control information therebetween. Certain ultrasonic testing information derived by the tester 44 and accumulated by the electronic control unit 38 may be stored at times on to a mass storage device 50 such as a conventional floppy disc cartridge system, for example. To provide operator interaction with the ultrasonic testing system, an operator interactive device 52 may be electrically coupled to the electronic control unit 38 using signal lines 54. The device 52 may be a keyboard/printer similar to the type manufactured by Texas Instruments, Model No. TI-700.

In operation, an operator initially calibrates the ultrasonic tester 44 and standard motor drive unit 30 in accordance with conventional calibration procedures which are well known to anyone skilled in the pertinent art of boresonic testing. Next, the operator enters through the interactive device 52 initialization test data information necessary for the adaptive control of the ultrasonic testing of the turbine rotor 24 into the electronic control unit 38. The operator may at the same time additionally select one of a plurality of control modes which may be characterized by a plurality of sets of programmed instructions in the electronic control unit 38. These control modes and their operational description will be provided in greater detail herebelow. Thereafter, the electronic control unit 38 governs the motor drive unit 30 to index the mechanical arm 20 through the rotor bore 22 at predetermined increments utilizing the signal lines 36. Upon the generation of an anomaly indication by the ultrasonic tester 44, which may be provided to the electronic control unit 38 by one of the signal lines 48, the control unit 38 may query the ultrasonic tester 44 for information related to the crystal transducer channel which received the back-reflected signal which is causing the anomaly indication, the amplitude level of the reflected signal which is causing the anomaly indication, and the measured time that it took the ultrasonic signal to propagate through the turbine rotor material and be reflected back to the crystal transducer from the potential imperfection in the rotor material 24. In addition to the test data received from the ultrasonic tester 44 as a result of the anomaly indication, the control unit 38 further queries the drive unit 32 to obtain the axial position and the angular orientation of the crystal transducer channel in question in the turbine rotor bore 22 utilizing signal lines 40. The test data acquired over signal lines 40 and 48 may be accumulated at such a high speed that it may not be necessary to suspend the operation of the mechanical arm 20 being indexed incrementally into the turbine rotor bore 22, in some cases. Still further, the electronic control unit 38 is additionally programmed to sequentially store the test data acquired over signal lines 40 and 48 in the mass storage device 50 and also print out this information in a desired format to the operator interactive device 52.

According to the control mode selected, the control unit 38 may either continuously govern the motor drive unit 30; or stop and maximize the amplitude level of the reflected signal which is causing the anomaly indication at each anomaly indication and then continue; or stop upon each anomaly indication and wait for a request to continue, generally activated by an operator. The electronic control unit 38 may continue to query, accumulate, store and record test data information provided over signal lines 40 and 48 with each anomaly indication, for example, until either all or a prespecified volume of the turbine rotor material 24 has been completely examined. At the end of the ultrasonic testing operation, a hard copy tabulated record of all of the test data is provided by the operator interactive device 52. In addition, a disc cartridge of the mass storage device 50, contains the test data information in a digital form suitable for telecommunication purposes utilizing a conventional modem coupled to the telephone system.

For the embodiment as shown in FIG. 1, the crystal transducers 28a, 28b and 28c may be arcuately disposed about the end 26 of the mechanical arm 20 equally separated by arcs of 120 degrees, for example. To further improve the ultrasonic viewing of potential imperfections in the turbine rotor material 24, one of the crystal transducers, say 28a, for example, may be positioned in a first plane which is perpendicular to the longitudinal axis of the mechanical arm 20, another of the crystal transducers, say 28b, for example, may be in a plane of a predetermined angle, say 60 degrees, for example, counterclockwise to the first plane, and the third crystal 28c may be in a plane which is of a predetermined angle, say 60 degrees, in a clockwise aspect to the first plane. In an alternate embodiment, the crystals 28b and 28c may be in planes oriented 45 degrees counterclockwise and clockwise to the first plane, respectively. In still another embodiment, the crystal transducers 28b and 28c may be oriented in planes with respect to the plane of 28a to view the turbine rotor material in a forward direction ahead of that rotor material volume being viewed by crystal transducer 28a. In these embodiments, the test data provided from the crystal transducers 28b and 28c which are not in planes perpendicular to the longitudinal axis of the mechanical arm 20 may be mathematically manipulated to obtain the true or effective location, amplitude and area of the potential imperfection in the turbine rotor material 24 causing the anomaly indication as detected by the ultrasonic tester 44. In these cases, the data which is stored in the mass storage device 50 and printed at the interactive device 52 are the computed effective test data values as described above. Further computational features of the electronic control unit 38 will become more apparent from the description provided in greater detail hereinbelow.

Figure 2:
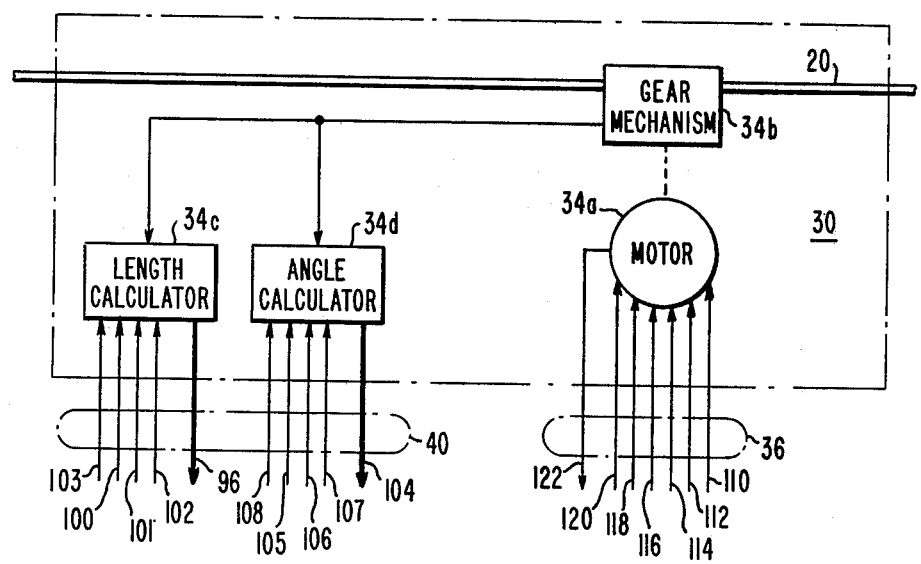
FIG. 2 is a block diagram schematic of a drive motor unit and interfacing signals suitable for use in the embodiment of FIG. 1.
Figure 3:
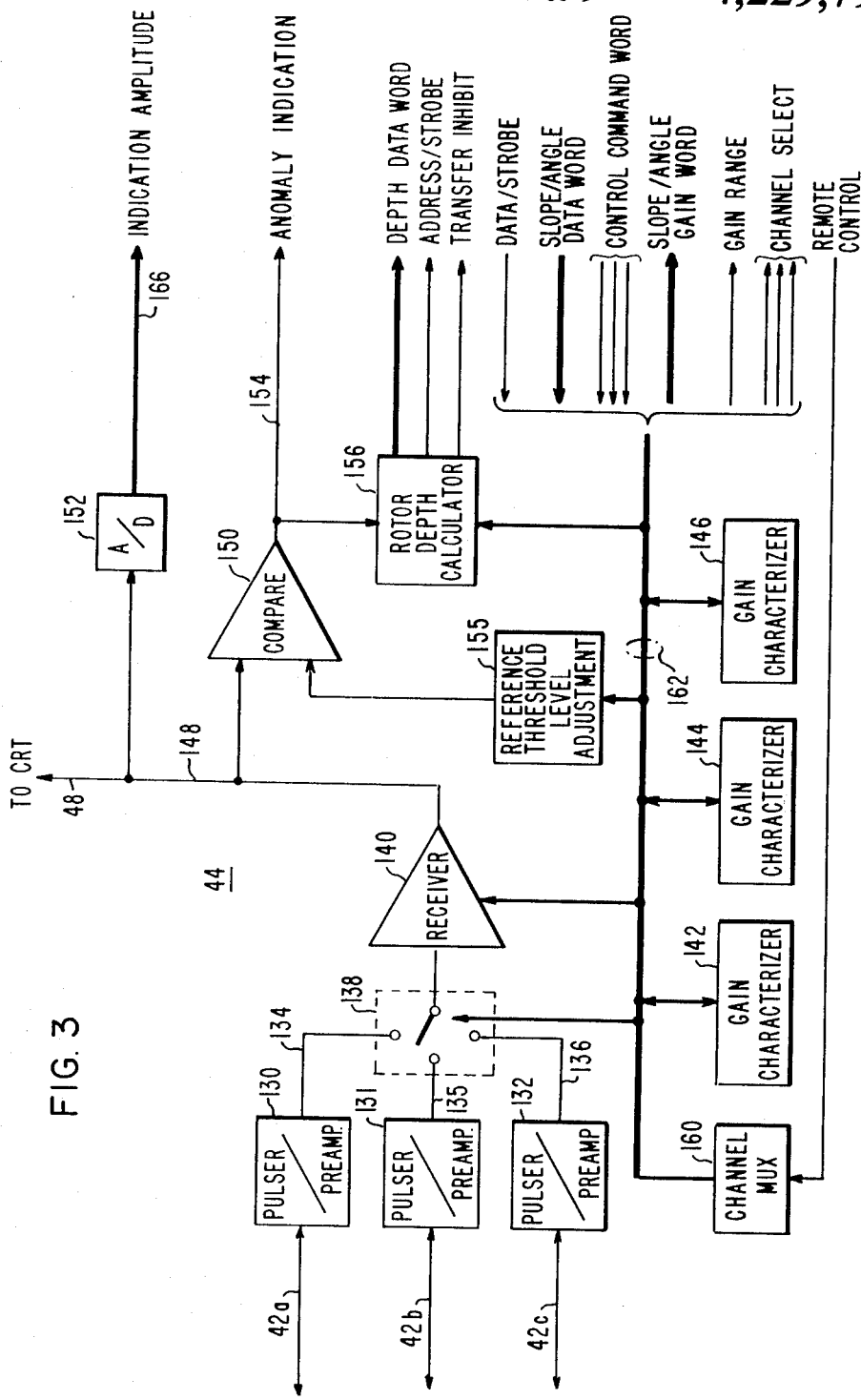
FIG. 3 is a block diagram schematic of an ultrasonic tester and interfacing signals suitable for use in the embodiment of FIG. 1.
Figure 5:
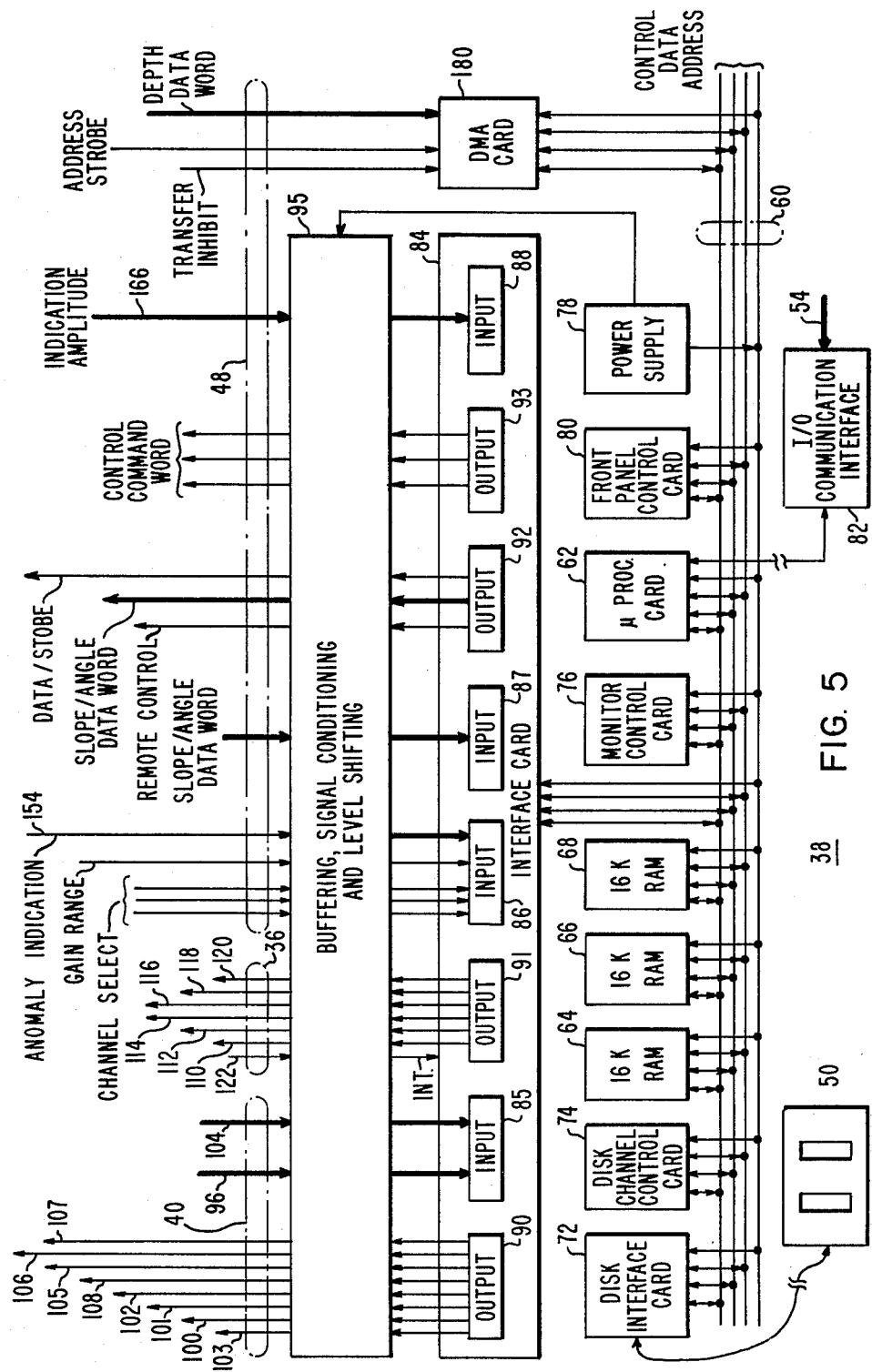
FIG. 5 is a schematic block diagram of a microprocessor-based electronic controller suitable for interfacing with the drive unit and ultrasonic tester embodiments of FIGS. 2 and 3, respectively, and for coordinating the ultrasonic testing operations thereof in accordance with the principles of the present invention.

The interactive coupling structure between the electronic control unit 38, ultrasonic tester 44, and motor drive unit 30 is provided more specifically in connection with the description of the combined FIGS. 2, 3, and 5. In FIG. 5 is shown a schematic block diagram architecture of the electronic control unit 38 which for the purposes of the present embodiment is a microprocessor-based digitally programmed unit operative to adaptively control the ultrasonic testing operations. The functional elemental components of the unit 38 may be comprised of system modules similar to those of the MDS800 Standard Development System manufactured by Intel Corporation. Each of the system elements in the electronic controller 38 may be coupled to a conventional microprocessor bus 60 comprising control, data, address, and power associated signal lines. At the heart of the electronic controller 38 is a central microprocessor unit 62 which may be similar to the SBC 80/10A single board microprocessor computer card manufactured by Intel Corporation. The microprocessor unit 62 is electrically coupled to the microprocessor bus 60 and interacts with a random access memory (RAM). The random access memory may be implemented in the form of RAM cards similar to the type manufactured by Intel Corporation Model No. SBC-016. A plurality of these RAM cards each containing 16K of memory are shown coupled to a microprocessor bus 60 at 64, 66 and 68. Generally, the microprocessor (not shown) included in the card 62 processes the plurality of sets of instructions and data words contained in the memory units 64, 66 and 68 to perform certain prespecified system and process operations as will become more apparent by the description provided below.

In one embodiment of the electronic control unit 38, a dual disc memory system 50 similar to the type manufactured by Intel Corporation Model No. SBC-212 is used as the mass storage device to store a plurality of programs comprising various operational instructions and data words, for example. In order to operably and electrically link the disc memory 50 to the microprocessor bus 60 so that it may cooperatively communicate with the microprocessor card 62 in accordance with associated instruction sets in the RAM units 64, 66 and 68, for example, certain interface and control electronics are necessary. This is accomplished in the present embodiment with the use of a disc interface card 72 and a disc channel control card 74 both similar to the type manufactured by Intel Corporation under the Model Nos. SBC-504 and SBC2DS, respectively. In addition to the interface and control electronics of 72 and 74, a monitor control card 76 is additionally supplied and coupled to the microprocessor bus 60. The monitor control card 76 which may be similar to the type manufactured by Intel Corporation contains a comprehensive disc system monitor which may reside in a plurality of read only memories contained on the card and provide the necessary loading, executing, and debugging instructions which cooperatively link the system operations between the microprocessor card 62, the memories 64, 66 and 68 and the disc system components 50, 72 and 74. The implementation and operation of these components are well known to one skilled in the pertinent art and reference is made to the well-known microprocessor manuals published by Intel Corporation for more detailed information in connection therewith.

Power may be supplied to the system component units of the electronic controller 38 by a power supply unit 78 which is conventionally supplied with the microprocessor family of system components such as the MDS-800 Microprocessor Development System manufactured by Intel Corporation. To allow for interactive system operation with the system components just described, a front panel (not shown in FIG. 5) may also be supplied with the MDS-800 System. To interact with the front panel, a front panel control card 80 couples the various push button and display elements thereof with the microprocessor bus 60 as is well known to those skilled in the pertinent art.

The interactive system components of the electronic control unit 38 will be described in connection with the embodiments of FIGS. 2 and 3. To begin with, a conventional I/O communication device 82 which may be a part of the microprocessor card 62, for example, is supplied to interact with the operator interactive device 52 which as indicated above may be a TI-700 silent typewriter type system. The communicative link 54 may be one of a standard current loop which is serially interrupted in accordance with digital words of a known digital format or may be one of a standard RS-232C interface, both operations being well known to anyone skilled in the pertinent art.

The majority of the digital I/O interface connections may be made through an interface card 84 which may be similar to the type manufactured by Intel Corporation bearing Ser. No. SBC-508. The interface card 84 may be conventionally coupled to the interface bus 60 to interactively and cooperatively function with the microprocessor card 62 in accordance with the processing of the preprogrammed instructional sets. The interface card 84 used for the preferred embodiment is divided into a plurality of 8-bit input and output modules. The plurality of input modules are denoted at 85, 86, 87 and 88. And, the plurality of output interface modules are denoted at 90, 91, 92 and 93.

Certain buffering, signal conditioning and level shifting may be required, at times, to interface the electronic control unit 38 to the ultrasonic tester 44 and motor drive unit 30. In these cases, electronic circuits such as that denoted in block 95 will be utilized for these purposes. These electronic circuits are conventional in nature and may be, for example, used to provide additional current or voltage required for driving a relay, for example, or may provide for certain level shifting between non-compatible digital input and output circuits such as that between transistor-transistor logic (TTL) and C-MOS logic, for example. Other conditioning may be that of filtering various input and output signals as a result of the external environment and activation mechanisms such as push buttons or relays, for example. Another aspect of conditioning may be where the interface signals between the testing units 44 and 30 and the control unit 38 are not synchronously timed in which case certain time buffering may be necessary. These interfacing type circuits such as that denoted by block 95 are conventional in nature and well known to anyone skilled in the pertinent art and in no way form any part of the present invention.

In describing the interface structure in more greater detail reference is made to both FIGS. 2 and 5. In FIG. 2, a conventional motor 34a is mechanically linked to known gearing mechansims 34b which adjust the movement of the mechanical arm 20. Coupled to the gearing mechanism 34b are an axial length calculator 34c and an angle orientation calculator 34d, both units being similar to that manufactured by Trionics, Inc. The axial length calculator 34c may be utilized in the present embodiment to provide the axial position of the crystal transducers at the end 26 of the mechanical arm 20 within the turbine rotor bore 22. This axial positioning data may be derived in the form of a number of binary coded decimal digits, say six, for example, each of a 4-bit format and may be transferred to the electronic unit 38 in a multiplexed fashion wherein a 4-bit data bus 96 is provided to the input interface module 85 as conditioned by the electronic circuits of 95. A plurality of address lines 100, 101, and 102 and a gate enable signal 103 are provided to the length calculator 34c from the output module 90. The digit display information conducted over line 96 relates directly to the address information supplied over signal lines 100, 101, and 102 and the gate enable signal 103. Similarly, the angle calculator 34d derives the angular orientation of the crystal transducers at the end 26 of the mechanical arm 20 at a particular axial index state in the form of a number of binary-coded-decimal (BCD) digits, say six digits, for example. The interface with the electronic control unit 38 is similar to that provided for the length calculator 34c wherein each BCD digit is multiplexed over the signal lines 104 in accordance with the address lines 105, 106, and 107 and the gate enable signal 108 which are all interfaced to the interface card 84 for the same output and input modules 90 and 85 respectively.

Interface lines which are output from interface module 91 and provided to control the motor 34a may be comprised of a motor start signal 110, a motor stop signal 112, a motor index forward signal 114, a motor index reverse signal 116, a set index ½ inch 118, and a set index ¼ inch 120, for example. In addition, a busy/done signal 122 which is indicative of the drive unit 30 indexing to the next axial position increment may be provided to an interrupt (INT) port of interface card 84. It is understood that the interface signals 36 used to control the motor 34a are merely exemplary of the type of motor control signals which may be used to control a conventional motor drive unit such as that described in connection with the embodiment of FIG. 2 and that modifications, additions and deletions to these type of interface signals to adapt the electronic control unit 38 to control another motor drive unit 30 may be made without deviating from the broad principles of applicant's invention.

To facilitate the description of the interface between the electronic control unit 38 and ultrasonic tester 44, a functional block diagram schematic of the ultrasonic tester 44 is provided in FIG. 3. Referring to FIG. 3, each signal line 42a, 42b, and 42c respectively electrically coupled to the crystal transducers 28a, 28b, and 28c are each attached to a pulser/preamplifier circuit 130, 131, and 132, respectively. These pulser/preamplifiers 130, 131, and 132, which are conventional to ultrasonic testers of the type described in connection with FIG. 3, each activate their corresponding crystal transducers 28a, 28b and 28c to periodically provide for a pulse of ultrasonic energy which is propagated through the turbine rotor material 24. And, during the time interval immediately subsequent to the pulse activation of the crystal transducers, the pulser/preamplifiers 130, 131 and 132 are operative in a receive mode to receive the back-reflective echo signals directly associated with the most recent ultrasonic pulse transmission.

The preamplified signals 134, 135, and 136 generated from the preamplifiers 130, 131, and 132, respectively, may be multiplexed by a multiplex switch function 138 into a conventional receiver amplifier unit 140. A digital gain characterizer is additionally supplied for each of the input channels 42a, 42b, and 42c. In the Tek Tran ultrasonic testers the gain characterizers, denoted by blocks 142, 144, and 146, may be of the type bearing the trade name DAC-10. Each of the gain characterizers 142, 144 and 146 may be synchronously multiplexed with a channel switch 138 to digitally control the gain of the receiver amplifier 140 in accordance with the received crystal transducer channel signal. The output signal 148 of the receiver 140 is supplied to one input of a comparator function 150, to an input of a conventional analog-to-digital converter 152 and also is supplied to the cathode ray tube (CRT) 46, not shown. A second input to the comparator function 150 is supplied from a reference threshold level adjustment circuit 155 and is operative synchronously with the timing of the channel multiplexer switch 138. The output of the comparator function 150 is an anomaly indication signal 154 which may be supplied to a rotor depth calculator circuit 156. A conventional electronic multiplexing timing circuit 160 controls the input signal channel multiplexing of switch 138 and synchronizes a selected one of the gain characterizer circuits, that is, either 142, 144 or 146, to digitally control the gain of receiver 140 in accordance with the selected input signal channel. Also, the reference threshold level adjustment is controlled in conjunction with the input channel selection by the channel multiplexer 160 to provide a respective reference threshold level signal to comparator function 150. The rotor depth calculator 156 is also governed in its calculations by the timing and address signals of the channel multiplexer 160 as will be described in more detail herebelow.

More specifically, the ultrasonic tester 44 of the present embodiment incorporates a bus structure denoted at 162 which may be comprised of the following signals: a 3-bit channel select address, a 1-bit signal denoting gain range, a slope/angle gain word which may be comprised of 4 bits, a 3-bit control command word, a 4-bit slope/angle data word, and a 1-bit data/strobe signal. In addition to these signals of the bus 62, the rotor depth calculator 156 generates an 8-bit depth data word, a 1-bit address/strobe signal and a 1-bit transfer inhibit signal. The utilization of these signals in connection with the interface of the electronic control unit 38 will become more apparent from the more specific description provided herebelow.

In operation, the channel multiplexer 160 may provide a 3-bit channel select signal identifying which channel has been chosen to be operated on by the receiver 140. The appropriate gain characterizer 142, 144 or 146 responds by providing the appropriate slope angle gain words to the receiver circuit 140. Both the reference threshold level adjustment circuit 155 and the rotor depth calculator circuit 156 respond to the channel select signal lines by respectively providing the appropriate reference threshold level signal to the comparator 150 and deriving the depth location in the rotor material with respect to the channel which has been selected.

The type of gain characterizer used in the present embodiment includes a digital memory which contains a gain related word in each of its registers. In the receiving time interval subsequent an ultrasonic pulse transmission, the receiver is operative to undergo a gain change for a predetermined number of incremental time intervals, say 99, for example. Each gain characterizer 142, 144 and 146 may be programmed in accordance with a preset number of time intervals. For example, say for the present embodiment, the number of time intervals may be considered as 5, in which case 5 of the registers in the gain characterizer will alter the gain of the receiver 140 for each preselected time interval. The output signal 148 from the receiver 140 will therefore be normalized and linearized in accordance with the preprogrammed gain changes. This output signal 148 is digitized by the analog-to-digital converter 152 to provide an 8-bit indication amplitude word 166. In another aspect of the ultrasonic tester 44, the rotor depth calculator 156 starts measuring time from a pulse transmission until an anomaly indication 154 is received at which time an output word denoted as depth data and an address/strobe signal are generated from the calculator 156. A transfer inhibit signal may also be generated by the rotor depth calculator 156 at times when no transfer of information is required.

Figure 4:
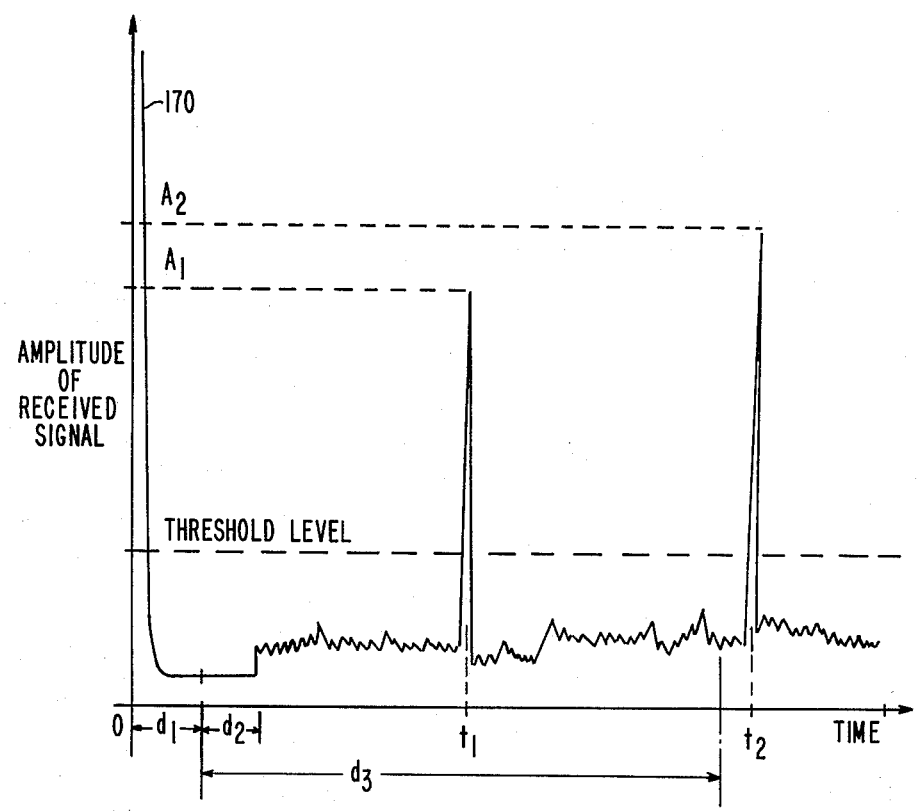
FIG. 4 is a sketch of a typical cathode ray tube (CRT) display scan of the back reflected echo signals in response to a transmitted ultrasonic signal wherein anomaly indications are generated.

A typical scan of the cathode ray tube (CRT) screen display depicting the received time interval just subsequent an ultrasonic pulse transmission is shown in FIG. 4. Normally, the sweep display of the screen is synchronized to the pulse transmission as shown at 170. The signal reception undergoes a number of delay times comprising the "water path" delay time $d_1$, the "gate start" delay time $d_2$, and the "gate stop" delay time $d_3$. During the interval between the delay times $d_2$ and $d_3$, reception of the back reflected echo signals through a selected channels are monitored by the ultrasonic tester 44 for anomaly indications and are displayed on the screen of the cathode ray tube. The amplitude level of most of the back reflected echo signals from any signal crystal transducer channel during this $d_2$-$d_3$ interval are usually of approximately the same level for a homogeneous turbine rotor material.

A threshold level which is usually provided to the comparator 150, is adjusted at a predetermined level above the amplitude of the reflection signals for the homogeneous turbine rotor material. This threshold level may be set at approximately 40% of the normalized amplitude range, for example. At times during the interval $d_2$-$d_3$ when a back reflected signal is greater than the threshold level, like that shown at time $t_1$, amplitude $A_1$, an anomaly indication is provided over signal line 154. At the same time the rotor depth calculator 156 measures the time from the pulse transmission at 170, for example, to time $t_1$ for the anomaly indication as shown in the exemplary scan of FIG. 4. The time $t_1$ and associated with the anomaly indication is proportionally representative of the depth within the turbine rotor material at which there is located the potential imperfection which is causing a reflected amplitude level $A_1$ greater than the predetermined threshold level. However, if a reflected amplitude level $A_2$ which is above the predetermined threshold level falls outside the $d_2$-$d_3$ interval like that shown at $t_2$ in FIG. 4, it will not cause an anomaly indication at signal line 154.

The interface coupling signals 48 between the ultrasonic tester 44 and electronic control unit 38 may be configured similar to that shown in connection with the microprocessor based embodiment of FIG. 5. Referring to FIG. 5, the 3-bit channel select, the gain range signal, and the anomaly indication signal 154, may all be coupled to the input interface module 86. In addition, the slope/angle data word and the indication amplitude data word 166 may be coupled to the input interface modules 87 and 88, respectively. The output interface module 92 may provide for the data/strobe signal and the slope angle data word and, in addition, a remote control signal which alters the operation of the channel multiplexer 160. Also, the output interface module 93 may be utilized to provide the 3-bit control command word to the ultrasonic tester 44. To further expedite the accumulation of test data as derived by the ultrasonic tester 44 in real time, a direct memory access (DMA) interface module 180 is additionally disposed within the electronic control unit 38 and coupled to the microprocessor bus 60. The direct memory access (DMA) module which may be a standard INTEL system component conventionally functions with the microprocessor card as directed by the INTEL MDS-800 system.

Digital signals such as the depth data word and the address/strobe digital bit may be accessed directly into the memory of the microprocessor based control unit 38 utilizing the functions of the DMA module 180. A transfer inhibit signal is additionally provided from the ultrasonic tester 44 to the DMA module 180 to inhibit transferring of test information from the DMA module 180 to the memory units of the electronic unit 38 for reasons peculiar to the ultrasonic testing operation.

The programming of the microprocessor-based electronic control unit 38, configured such as that shown in FIG. 5, may be organized into a number of functional modules. Programs related to peripheral handlers and system program communications may utilize the hardware manufacturer's operating system software which in the case of the preferred embodiment may be that of INTEL Corporation's MDS-800 system. The functional programmed modules and operating system may be organized and controlled by an executive routine similar to that shown in the flowchart of FIG. 6. Tabulated herebelow are the typical names of the program modules for use in the microprocessor-based embodiment of FIG. 5.

| PROGRAM MODULES | |
|---|---|
| Initialize | (INIT) |
| Communications | (COM) |
| Stop-On-Indication | (SOI) |
| Scan | (SCAN) |
| Maximize | (MAX) |
| Adjust | (ADJ) |
| Math | (MATH) |
| Eight | (EGT) |
| Save | (SAV) |
| Diagnostic | (DIG) |
| Direct Memory Access | (DMA) |
| Interrupt Service | (ISR) |

For the purposes of the present embodiment, the program modules which may be provided by the hardware manufacturer's operating system software package associated with the MDS-800 system include Initialize, Communications, Diagnostic, Direct Memory Access, and Interrupt Service. The remaining application program modules such as Stop-On-Indication, Scan, Maximize, Adjust, Math, and Eight, may be programmed into the memory of the microprocessor-based system in accordance with the flowcharts shown in FIGS. 7 through 11.

A brief description of the program modules associated with the disc operating system of the hardware manufacturer such as Intel Corporation, for example, is provided now for the purposes of better understanding the operation of the various hardware system components. To start with, the Initialize program module, when activated, may put the registers in the interface hardware, such as that shown at 84 in FIG. 5, in their required initial state and in addition perform other system clearing and register setting operations which are well known to a person skilled in the use of microprocessor-based systems. The Initialize program module may also notify the operator of system start-up and request instructions and test data information from him. Based on the operator's input, program execution will be continued at a selected starting point in the executive program. The Communications program module may comprise basically two parts, namely a handle console I/O, and a disc I/O. The handle console I/O portion may be comprised of both general purpose messages and formatted data strings and further include operating system interface software which will permit interaction with the operator interactive device 52. The disc I/O portion may permit the reading or writing on the disc system 50 in accordance with certain predetermined program segments which may be required to organize the data transfer. The Save program module may be utilized to organize process data in a proper format and cause it to be stored on the disc system 50. It may also provide a listing of the test results on the console unit 52 and still further, it may provide control system functions for the orderly termination of data collection and storage. The Diagnostic program module may be a collection of subroutines which allow an operator to determine that the hardware is basically functional. The Direct Memory Access program module may provide handling of the high speed transfer of data from the ultrasonic tester 44 to the memory of the electronic control unit 38. Usually, the transferred data set is routed to a preassigned area in memory for further manipulation by other program modules. Finally, the interrupt service program module may direct program execution in response to system interrupts including front panel and operator initiated ones.

Figure 6:
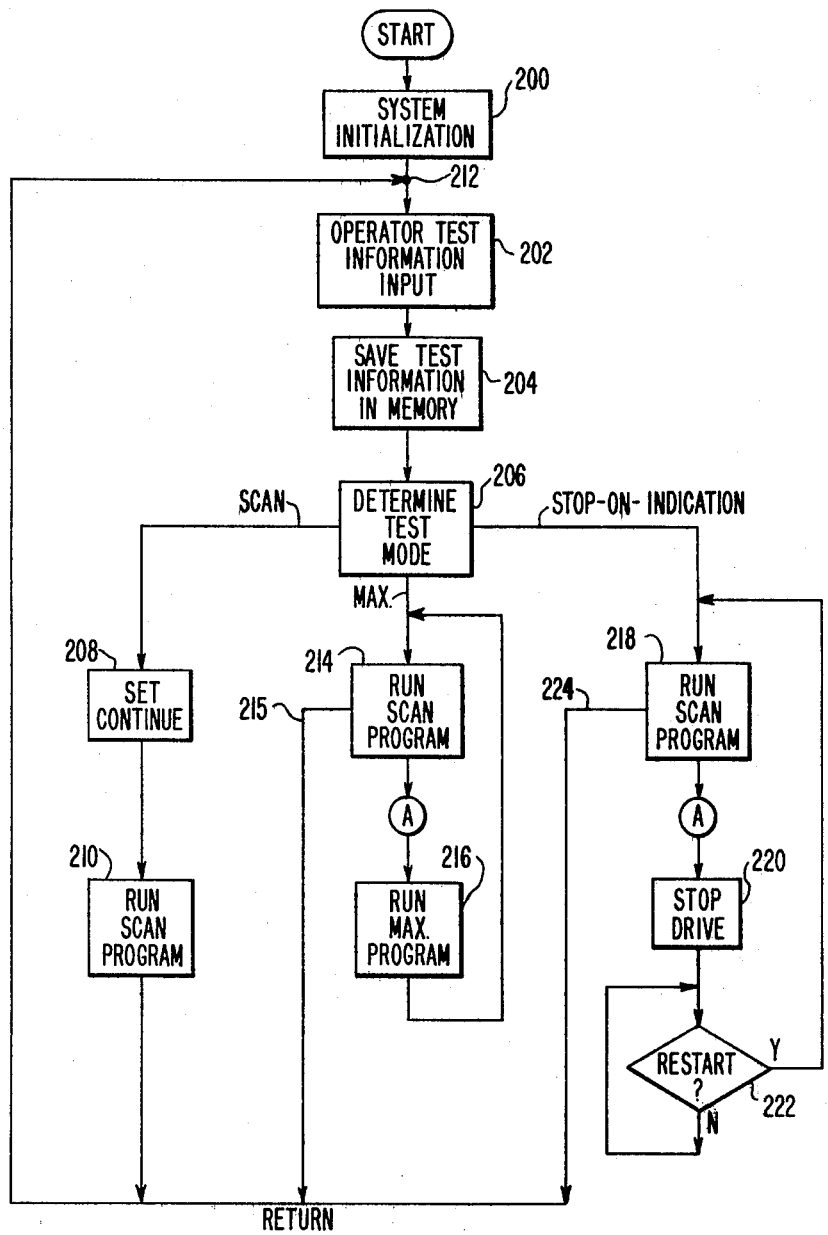
FIGS. 6 through 11 are flowcharts depicting a typical sequential processing operation of the electronic controller embodiment of FIG. 5 and suitable for use in programming the plurality of sets of instructions and data digital words in the memory unit thereof.

Referring to the executive program flowchart of FIG. 6, after the electronic control uit 38 is started up by an operator activation such as a pushbutton depression on an operator's front panel, executive program execution begins at block 200. Since in the preferred embodiment a disc operating system is used, the system initialization block 200 initiates the loading of the memory modules 64, 66, and 68 with the programs which are stored on the disc system 70 utilizing the disc interface and disc channel control parts 72 and 74, respectively, and the monitor control card 76. Thereafter, all of the appropriate hardware registers are initialized to their starting points. Throughout the following description, the operating system program modules described above will be utilized by the application program modules but will not be referred to directly. It is understood that any person skilled in the microprocessor programming art will understand when and how these programs are called for and executed as related to the functions which are described in the application program flowcharts here to follow. Continuing through the flowchart of FIG. 6, the next block of instructions 202 queries the operator for input test data information necessary for conducting the ultrasonic testing of a test rotor specimen. A typical example of operator input information as queried by the operator interface device 52 is shown in Table I.

TABLE I

Typical Operator Test Data Input

DATE: ?
PLACE OF TEST: ? CHARLOTTE N.C.
OPERATOR: ? AEH
S.O. NO.: ? 5432
DRAWING NO.: ? 137J467
TEST NO.: ? TN12345
PURCHASE ORDER NO.: ? 51-7E-207331-MM1
UT UNIT SERIAL NO.: ? E-83459
TEST TYPE: (SCAN) (MAX) (SOI)? SCAN
ALARM THRESHOLD: ? 40
REF. END: (GOV) (GEN)? GEN
XTAL CORRECTION: (Y/N)? NO
XTAL CORRECTION: (Y/N)? N
COMMENTS: ? HI YALL
BORE DIAMETER: ? 8.32
STARTING AXIAL LENGTH: ? 0.00
STARTING ANGLE: ? 0
ENDING AXIAL LENGTH: ? 86
XTAL INFO.:
CHAN: 1
ANGLE: ? 0
DIRECT.: ? LONG
ROOF: ? 8'
DIA: ? 3
HOLE: ? F
DEPTH: ? .125,,,,,.225001..1,1.50,2.50
% FS: ? 50
  OTHER: ? NONE
CHAN: 2
ANGLE: ? 60
DIRECT.: ? CW
ROOF: ? 0
DIA: ? 8
HOLE: ? S
DEPTH: ? .500,1.00,2.00,4.00,8.00
% FS: ? 80
10 OTHER: ? UNDMP
CHAN: 3
ANGLE: ? 60
DIRECT.: ? CCW
ROOF: ? 0
DIA: ? 8
HOLE: ? S
DEPTH: ? .500,1.00,2.00,4.00,8,,.00
% FS: ? 100
% FS: ? 99
  OTHER: ? UNDMP
TYPE "RETURN" TO START TEST

After this, operator input information is stored in both the temporary memories of 64, 66 and 68 and the disc system memory 50 as provided by the execution of the instructions of block 204; program execution then continues at block 206. In block 206, the control unit 38 determines which one of a plurality of control modes has been selected by the operator in block 202. Exemplary of these control modes are SCAN, MAX, and STOP-ON-INDICATION, for example.

If the SCAN control mode is selected, for example, a continue flag will be set by instructional block 208 and the Scan program module will be executed in block 210. Upon completion of the ultrasonic testing of the rotor specimen, program execution exits the Scan program and returns to point 212 in the executive routine of FIG. 6 to wait for new operator test input data. If the MAX control mode is selected, the Scan program module is executed in block 214. The Scan program module has two exiting points. One exiting point 215 returns the program execution to point 212 and the other program exiting point denoted as Ⓐ continues program execution at block 216 wherein the Max program module is executed. After executing the Max program module, the program execution is returned to the Scan program at block 214. Programs Scan and Max are repetitively and sequentially executed in blocks 214 and 216 until the ultrasonic testing of the rotor specimen is complete and the Scan program is exited at line 215. If the STOP-ON-INDICATION control mode is selected by the operator in block 202, then program execution continues at block 218 wherein the Scan program is executed. When the Scan program is exited at point Ⓐ the next sequential instruction 220 stops the motor drive unit 30. Program execution then sits in a wait loop at decisional block 222 for an operator initiated restart indication. Upon reception of a restart indication, the program execution continues at block 218 in which the Scan program is re-executed. The sequential execution of instructional blocks 218, 220 and 222 continue until the ultrasonic testing of the rotor specimen is complete, at which time the Scan program exits at line 224 and returns the program execution to point 212 in the executive routine. New operator test input information may then be supplied for the next rotor test specimen.

Figure 7:
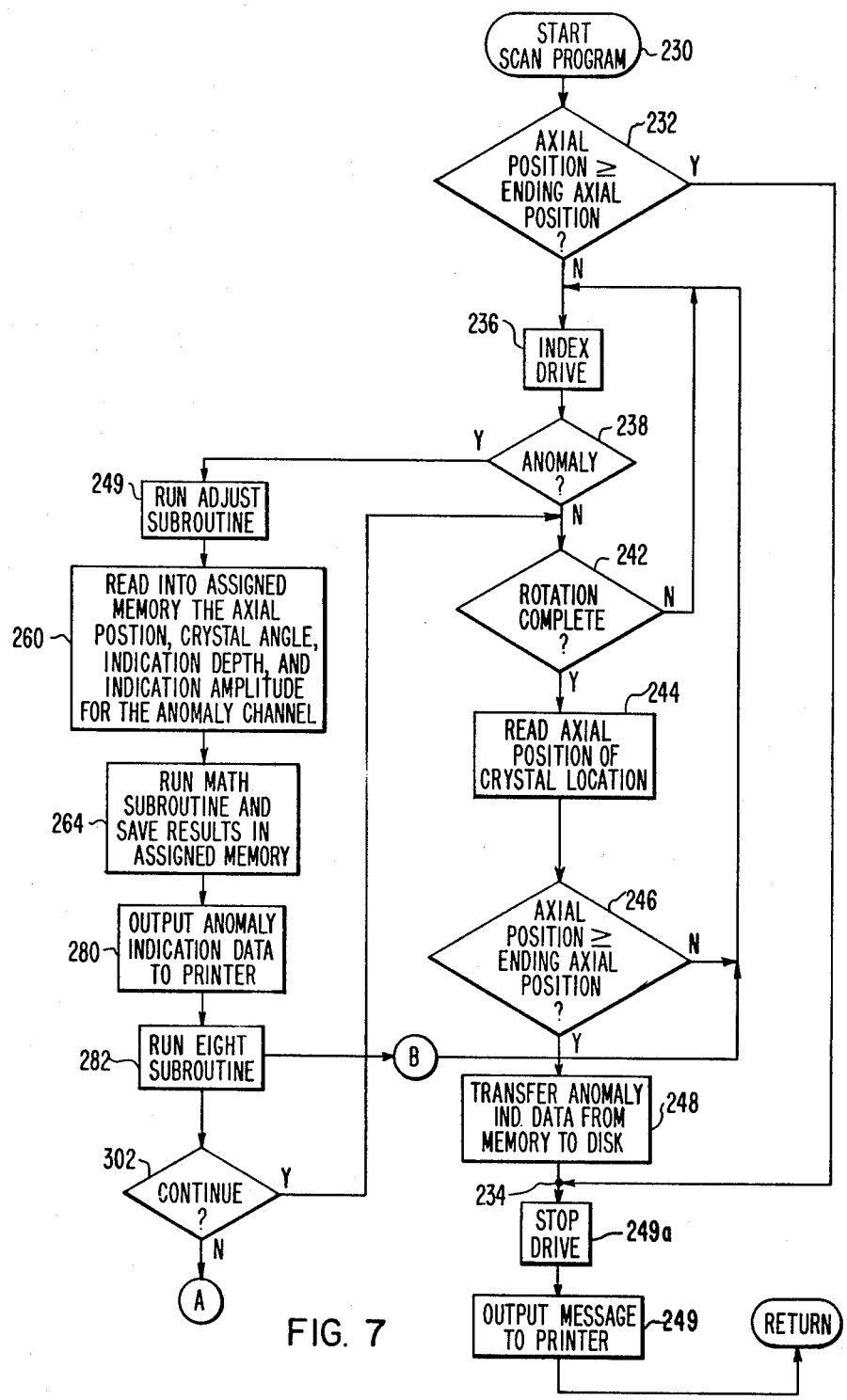

The Scan program may best be described in connection with the exemplary flowchart of FIG. 7. The Scan program is initiated at block 230. In block 232, the present axial position, which has been entered into memory by use of the interface lines 100–103 and 96, is compared with the ending axial position value provided as part of the test input information from the operator's console 52. In block 232, if it is determined that the present axial position is greater than or equal to the ending axial position value than program execution is continued at point 234. Otherwise, the motor drive unit 30 is indexed in block 236 utilizing interface lines 110–122. In instructional block 238, the control unit determines if an anomaly indication is present on signal line 154. If there is no anomaly indication present, the controller at decisional block 242 then determines if the plurality of crystal transducers have been completely rotated through the predetermined arc, say 375°, for example, about the longitudinal axis of the mechanical arm 20 by monitoring the busy/done signal line 122. If not, the motor drive indexing is continued at instructional block 236; otherwise, the present axial position of the crystal transducer location within the rotor bore is read into the controller utilizing signal lines 100–103 and 96 in accordance with the executed instructions of block 244. Thereafter program execution is continued at instructional block 246 wherein the present axial position of the crystal transducers within the rotor bore 22 is again compared to the ending axial position value submitted by the operator. If the present axial position is greater than or equal to the ending axial position, all of the test data read in as a result of the anomaly indications are transferred from the temporary memory denoted at 64, 66 and 68 to the disc system 50 utilizing the appropriate operational program modules described briefly above. Thereafter, program execution is continued at point 234. If the present axial position is less than the ending axial position as determined by block 246, the drive motor unit 30 is again indexed by block 236.

Figure 10:
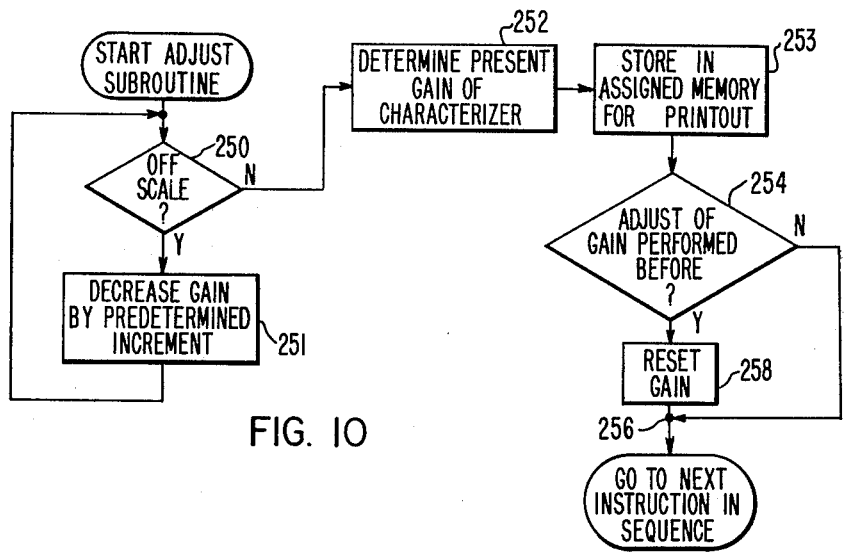

When an anomaly indication is present over signal line 154 as determined by decisional block 238, the Adjust subroutine is next executed. The flowchart displayed in FIG. 10 is typical of an Adjust subroutine suitable for use in the present microprocessor based system embodiment. The Adjust subroutine of FIG. 10 starts at decisional block 250 wherein it is determined if the present indication amplitude as read in over signal lines 166 is greater than a predetermined 100% scale setting. If so, the gain of the gain characterizer 142, 144 or 146 (see FIG. 3) associated with the crystal transducer channel causing the anomaly indication is decreased by a predetermined gain increment in instructional block 251. The interface lines comprising the control command word, the slope/angle data word, the remote control signal, and the data/strobe signal are utilized for changing the gain of the appropriate gain characterizer. After the digital gain of receiver 140 has been incrementally decreased decisional block 250 again determines if the present indication amplitude over signal lines 166 is still off scale. If so, instructional block 251 is repeatedly executed until decisional block 250 indicates that the indication amplitude is within the scale range. Once this is determined, program execution continues at instructional block 252 wherein the present gain of the gain characterizer which has just been altered is determined with respect to some known calibration gain value, normally computed as a proportional number of gain increments. For example, if it took 19 gain decrements to cause the amplitude to fall within the normalized scale setting and if it is known through calibration techniques that 28 gain decrements represents $-6db$, then the gain has been reduced by $(19/28) \times 6db$. Thereafter, the gain value determined by block 252 is stored in a preassigned portion of memory for printout by block 253. Next, decisional block 254 determines if the gain of a gain characterizer has been adjusted. If it has not, the program execution is exited at point 256; otherwise, the gain of the gain characterizer, which has been altered by block 251, is reset to its original value in instructional block 258 and then the Adjust subroutine is exited at point 256.

In the next instructional block 260 of the Scan flowchart, the present values of the axial position over lines 96, the crystal angle rotational value over lines 104, the indication depth utilizing the DMA module 180, the indication amplitude over signal lines 166, and the crystal channel, causing the anomaly indication, read from signal lines denoted as channel select are all read into an assigned portion of the temporary memory which may be in one of the memory cards 64, 66 or 68.

Figure 9:
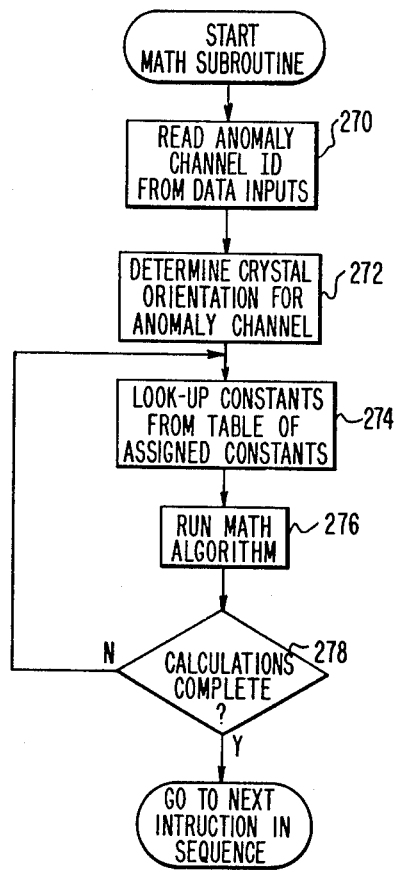

In the next instructional block 264, the Math subroutine is executed to correct the data read in from instructional block 260 to derive the true or effective indication amplitude, location and area of the anomaly indication in the turbine rotor material. A typical example of a Math subroutine suitable for use in the present embodiment is depicted in the flowchart of FIG. 9 wherein the anomaly channel ID is determined by functional block 270 which initiates the sequence of instructions of the Math subroutine. In the next instructional block 272, the angle of crystal orientation for the anomaly channel at the time of the anomaly indication is also read into the Math subroutine. In the next two sequentially executed instructional blocks 274 and 276, a number of look-up constants are obtained from a table of assigned constants and a math algorithm is executed. Typical values of the constants which are preprogrammed into the table of assigned constants and the type of math algorithms executed in block 276 are displayed in Table II for a better understanding and description thereof.

TABLE II

Typical Algorithms Executed In Math Subroutine

| Crystal Detecting Anomaly | Correction |
|---|---|
| 60° clockwise | 1. Add $\theta$ to angular position |
| | 2. Multiply anomaly depth by 0.5 |
| 60° counter clockwise | 1. Subtract $\theta$ from angular position |
| | 2. Multiply anomaly depth by 0.5 |
| 45° forward | 1. Add product of anomaly depth and 0.707 to bore depth |
| | 2. Multiply anomaly depth by 0.707 |
| 45° aft | 1. Subtract product of anomaly depth and 0.707 from bore depth |
| | 2. Multiply anomaly depth by 0.707 |
| Channel Detecting Anomaly | |
| 1 | None |
| 2 | Add 120° to angular position and subtract 360° if result is greater than 360° |
| 3 | Add 240° to angular position and subtract 360° if result is greater than 360° |

$\theta$ = arctan (D 0.866)/(R + D 0.500)
D = anomaly depth; R = bore radius
Anomaly area will be determined by multiplying calibration area by a constant derived from percent full-scale anomaly amplitude.

Decisional block 278 determines when all of the calculations of the Math subroutine are complete and exits the Math subroutine to the next instruction or block 264 in the Scan program sequence which saves the results obtained from the Math subroutine program module into an assigned area of memory.

The next instructional block 280 of the Scan flowchart outputs the anomaly indication test data to the printing device of the operator interactive module 52. Thereafter, the subroutine entitled Eight is executed in instructional block 282. The Eight subroutine functionally controls the motor drive unit 30 when a predetermined number of anomaly indications are identified as occurring within a predetermined adjacent distance of each other and within the same angular orientation range which is characteristic of a long crack or continuous imperfection in the rotor material. For example, if two anomaly indications are detected within a program defined angular range of crystal transducer rotation and within an axial dimension interval of 1 inch, the motor drive unit 30 will be adapted to index at ⅛ inch increment instead of ¼ inch increments. In the above example, the crystal transducer head assembly 26 of the mechanical arm 20 may be repositioned to an axial position of ¼ inch upstream of the first anomaly indication location in the series of anomaly indications within the predetermined distance. Scanning may then proceed in ⅛ inch increments for a closer inspection of the rotor material volume associated with the uncovered axial dimension interval within the angular orientation range until two successive rotations do not detect another anomaly indication. Thereafter, the motor drive unit 30 may be reverted back to the normal ¼ inch incremental indexing mode.

Figure 11:
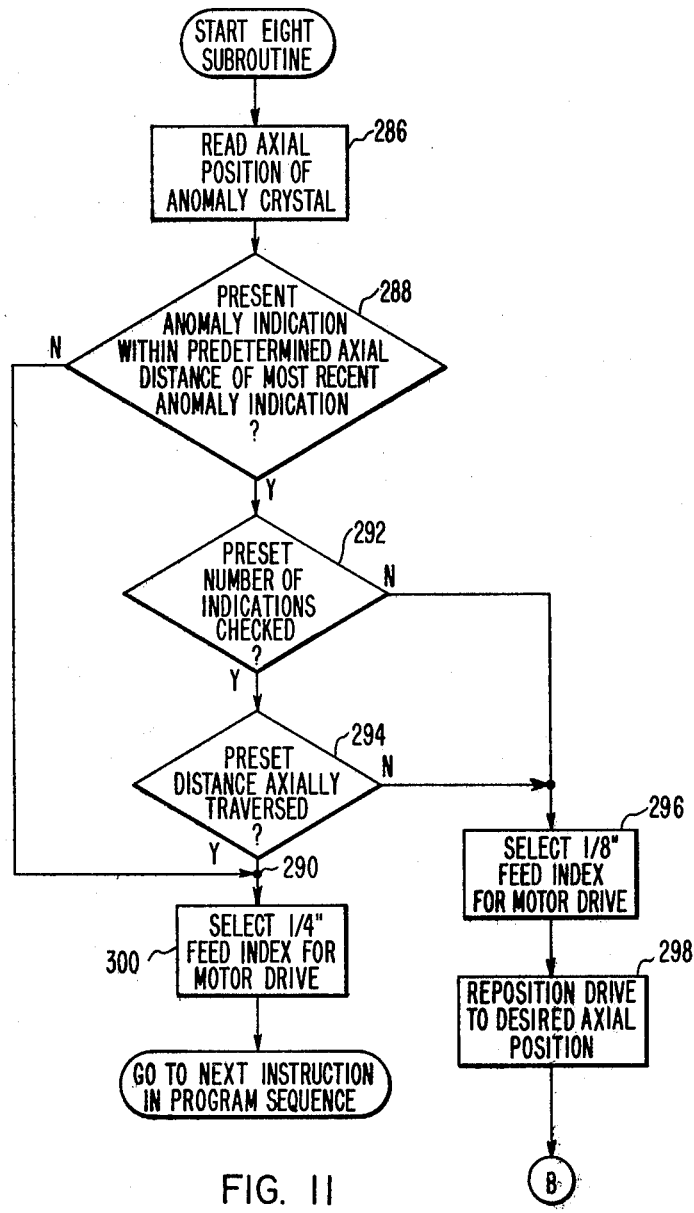

A typical example of the Eight program module may be described in connection with the flow chart of FIG. 11. In the initial instructional block 286 the axial position of the crystal causing the anomaly indication is read into the controller memory in the usual manner. In the decisional block 288, it is determined if an anomaly indication location is within a predetermined axial distance of the location of the most recent anomaly indication for the same angular orientation range of crystal transducer rotation. If this is not so, program execution is continued at point 290; otherwise it is determined in decisional block 292 if a preset number of indications have been checked. If they have, then it is determined in the decisional block 294 if a preset distance has been axially traversed within the same angular orientation range. If both 292 and 294 are true, program execution continues at 290. If both 292 and 294 are false, program execution continues at the instructional block 296. In block 296, the feed index for the motor drive unit 30 is selected to be ⅛ inch increments. In the next instructional block 298, the drive unit 30 is requested to reposition the mechanical arm 20 to a desired new axial position as described above. Thereafter, program execution is continued at the point denoted by Ⓑ.

From the program execution point 290 of the Eight flowchart, instructional block 300 selects a ¼ inch increment for the feed index of the motor drive unit 30. The Eight subroutine is then exited to the next instruction in the Scan program sequence. Referring back to the Scan program flowchart of FIG. 7, if the Eight subroutine is exited at a point designated as Ⓑ, program execution continues at instructional block 236 where the motor drive unit 30 is continued to be indexed. Otherwise, program execution continues at decisional block 302 where it is determined if the continue flag has been set. In the Scan control mode, the continue flag is set, causing the program execution to continue at instructional block 242. For all other control modes, the program execution continues as that point denoted as A.

Figure 8:
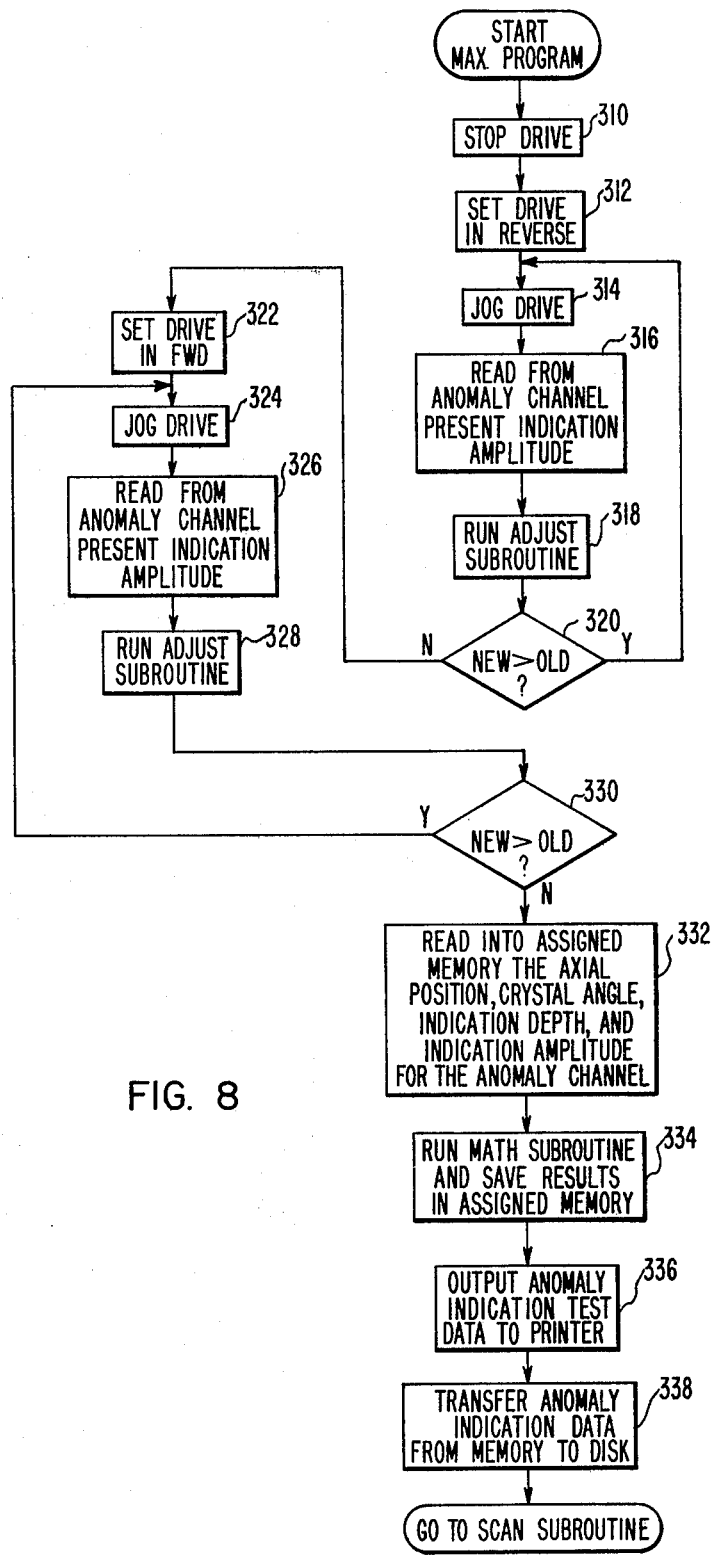

According to the executive program as denoted by the flow chart in FIG. 6, the MAX control mode is the only selected control mode which utilizes the MAX program module which is initially executed at instructional block 216. An example of a Max program module suitable for use in the embodiment as shown in FIG. 5 is described in connection with the flow chart displayed in FIG. 8. Referring to FIG. 8, the Max program module starts with an instructional block 310 which causes the motor drive unit 30 to stop utilizing the interface control lines 110 and 112. In the next instructional block 312, the drive motor unit 30 is set to index in reverse as controlled by the interface signals 114 and 116. The motor drive unit 30 is then intermittently requested to start by pulsing interface line 112, for example, in a joglike fashion by the instructional block 314. Concurrently therewith, instructional blocks 316 and 318 read in the present indication amplitude resulting from the anomaly indication and execute the Adjust subroutine, respectively. Thereafter, in the instructional block 320, it is determined if the present indication amplitude is greater than the most recent indication amplitude. If so, the drive motor unit 30 is continued to be controlled in a joglike fashion by instructional block 314; otherwise, the motor drive unit 30 is set to index in a forward direction by controlling the interface lines 114 and 116 in the instructional block 322. The motor drive unit 30 is again driven in a joglike fashion by the instructional block 324. During the jogging operation, the instructional blocks 326 and 328 read in the present indication amplitude caused by the anomaly indication and execute the Adjust subroutine. Thereafter, it is determined, in decisional block 330, if the present indication amplitude is greater than the most recent read in indication amplitude. If this is the case, the motor drive unit 30 is again jogged in the forward direction by instructional block 324; otherwise, test data such as the axial position, the crystal transducer rotation angle, the present indication depth in the rotor material and indication amplitude are all read into predetermined assigned memory for the channel which is causing the anomaly indication by the execution of instructional block 332.

Next, block 334 executes the math subroutine which operates on the test data which has been previously read in by block 32 and the results are again saved in another predetermined portion of the memory. The instructional block 336 then prints out to the operator's console 52, the anomaly indication test data which has been computed and saved in the memory by block 334. In addition, the test data which has been computed by the instructional block 334 is also transferred to a preassigned portion of the memory in the disc system 50 utilizing the conventional disc I/O operating system software and the hardware modules 72 and 74. The program execution is then continued at the SCAN program module executed in block 214. It is understood then that after it has been identified that the ultrasonic testing portion of the rotor specimen is complete the SCAN program stops the motor drive unit 30 at block 249a and outputs a message to the operator's console at block 249 and exits to point 212 in the executive program where the electronic control unit 38 will again query the operator for the next set of test data information.

An example of the test data format as it is printed out to the operator's console 52 in accordance with the execution of the instructional blocks 280 or 336 is shown in Table III.

Typically, the printout comprises a heading section which provides the conditions under which the test is being conducted. Following the heading portion, is a printing section which describes the orientation of the crystal transducers arcuately disposed about the inserting head of the mechanical arm 20 during the length of the test. The test data is provided below this section and may be printed out, in some cases, as the anomaly indications are identified and as the effective computations are conducted by the math subroutine. Each anomaly indication may be numbered as it sequentially occurs during the testing operation. As has been described hereabove, this test data which is printed out on the operator's console 52 is also stored in a memory disc cartridge in the disc system 50.

One purpose for storing test data on a disc cartridge is that the disc cartridge is portable and may be also utilized in another disc drive system which may be coupled to a conventional modem data storage and data communication device such as that manufactured by Micon Industries. The data communication device may include an acoustical coupler such that the accumulated test data may be transmitted to a central location expediently over dedicated telephone lines for that purpose. It is understood that the test data may be stored on the disc cartridge in accordance with the requirements of the modem data storage and data communication device. In one known device, the test data may be conveniently stored in single density using a standard IBM format. It is further understood that the central station may demodulate the test data information transmitted thereto and print the information onto an operator's console or other such device located thereat. Even further, in some cases the central station may manipulate the test data in-line as it is being received for the purpose of analysis and expeditiously retransmit its

TABLE III

| Typical Printout Of Ultrasonic Test Data |
| --- |

Heading:
Date:
Place of Test: 58 characters
Operator: 60 characters
Vendor No.: 58 characters
Drawing No.: 58 characters
Test No.: 50 characters
Purchase Order No.: 51 characters
UT Unit Serial No.: 51 characters
Test Type: (SCAN) (MAX) (SOF) (COP) - one only
Alarm Threshold: XX %
Comments: 60 characters
Bore Diameter: XX.XXX IN.
Starting Depth: XXX.X IN.
Starting Angle: XXX DEG.
Ending Depth: XXX.X IN.
Xtal Info.:

| | Entry | | | Calibration | | | | |
| --- | --- | --- | --- | --- | --- | --- | --- | --- |
| Chan: | Angle: | Direction: | Roof: | Dia: | Hole: | Depth: | % FS: | Other |
| 1 | XX | CCW | XX | XX | F | XX.XXX | XX | DAMP |
| | | CW | | | S | | | UNDMP |
| 2 | | FOR | | | | | | HIRES |
| | | AFT | | | | | | ANY 5 |
| | | LONG | | | | | | CHARACT. |
| | | | Total Xtal info lines not to exceed 15 | | | | | |

| Test Data: | | | | | | | | |
| --- | --- | --- | --- | --- | --- | --- | --- | --- |
| Indication No.: | Bore Depth: | Angle: | Anomaly Depth: | Amp: | Chan: | dB: | Area $IN^2$ | |
| 001 | XXX.X | XX | XX.XX | XX | X | XX | X.XXXXX | |
| " | " | " | " | " | " | " | " | |
| " | " | " | " | " | " | " | " | |
| " | " | " | " | " | " | " | " | |
| 999 | | | | | | | | | computed results back over the same telephone line to the modem data storage and data communication device located at the ultrasonic testing site. The test operators may then receive very quickly the turbine rotor material analysis results with respect to the severity of the identified anomaly indications and make appropriate decisions based on this information. Therefore, the apparatus used to accumulate the test data benefits the turbine rotor user by making his turbine rotor available more quickly.

In a typical operation, prior to operating the ultrasonic testing system embodiment as shown in FIG. 1, a test operaor may conduct a number of calibration operations according to well-known calibration procedures. In addition, during the calibration procedure, the crystal transducers may be disposed in their desired arc positions at the inserting head 26 of the mechanical arm 20. After the test operator determines the test conditions under which the particular rotor specimen is to be tested, he activates the electronic control unit 38 which automatically turns over control of the ultrasonic testing operation to the executive routine as particularly shown on FIG. 6. The executive routine enters the vital program modules into the RAM modules 64, 66, and 68 and also performs the desired initialization of the hardware registers within the electronic control unit 38. Thereafter, the electronic control unit queries the operator utilizing the operator console 52. At this time, the operator may input test data through the operator's console 52 in a manner and of the type which is shown in Table 1 hereabove. After this is accomplished, the electronic control unit 38 automatically receives and stores this input test information in assigned portions of the random access memory. The executive routine then determine which control mode has been selected by the operator from his input test data.

If we assume that the SCAN control mode has been selected, a continue flag will be set and the SCAN program module will be executed. The motor drive 30 is governed to start indexing the mechanical arm 20 through the rotor bore 22 and concurrently, the ultrasonic tester 44 is governed to activate the crystal transducers to propagate ultrasonic energy into the turbine rotor material 24 and receive the back-reflected echo signals. When an indication amplitude of an echo signal is determined to exceed the threshold level associated therewith, an anomaly indication occurs, similar to that shown at $t_1$ in FIG. 4. The electronic control unit 38 responds by determining first if the indication amplitude such as $A_1$ (see FIG. 4) is out of limits. If it is, the gain characterizing portions of the ultrasonic tester 44 are adjusted appropriately to bring the amplitude within scale. Otherwise, the axial position of the mechanical arm, the crystal orientation angle, the indication depth and amplitude are read into preassigned portions of the memory. Then, when required, the Math subroutine is executed to compute the effective values of the anomaly location, amplitude and area in the turbine rotor material. The results of the converted test data are also saved in other preassigned portions of memory. This test data information is also printed out on at least one line of the operator's console 52 similar to that shown in Table III. For example, the indication number is printed in the first column, the axial bore depth in the second column, the angle in the third column, the anomaly depth within the rotor material in the fourth column, the amplitude in the fifth column, the crystal transducer channel which received the anomaly indication in the sixth column, the amplitude in decibels in the seventh column, and the effective area of the anomaly location within the rotor material in the eighth column.

The Eight subroutine is then executed to determine if successive anomaly indications are within a predetermined adjacent distance of each other for the same angular orientation range. If this is the case, the motor drive unit 30 is repositioned behind the first of the anomaly indications of the detected sequence and the index is readjusted to $\frac{1}{8}$ inch increments, for example. The drive motor unit 30 is then indexed through the anomaly indications of the detected sequence at $\frac{1}{8}$ inch increments. If this is not the case, the electronic control unit 38 will proceed by continuously indexing the mechanical arm 20 through the turbine bore at $\frac{1}{4}$ inch increments, for example, and identifying the other anomaly indications which may be present. Each of the anomaly indications will be printed out on the operator's console and stored in the disc memory cartridge 50 for each of the anomaly indications present during an ultrasonic test. The test under the SCAN control mode may be conducted continuously without operator intervention.

Should the test operator select the MAX control mode with his test input information, the instructional function at 206 conducts the program execution to run the Scan program at functional block 214 except that the continue flag is not set. In this case instead of the Scan program being re-executed with each anomaly indication, a Max subroutine is inserted into the re-execution program loop. Each time an anomaly indication is detected the location of that anomaly indication is determined by maximizing the indication amplitude in accordance with the execution of the Max program module in block 216 shown in the executive program flowchart of FIG. 6. The printout of the test data may be similar to that shown in Table III upon detecting each anomaly indication. After that portion of the rotor specimen which has been prespecified for ultrasonic testing is complete, the MAX control mode is exited at 215 and returns to the executive program control at 212 waiting for the test operator to enter new test input information.

In the case in which the test operator selects the STOP-ON-INDICATION control mode, the Scan program module is again executed in block 218 similar to that executed by blocks 214 and 208. The exception being in this executive branch that when an anomaly indication is determined the motor drive unit 30 is stopped at block 220. No continuance of the ultrasonic test is permitted without operator intervention or an operator restart activation, which is shown at 222. Thereafter, the Scan program continues indexing the mechanical arm 20 and crystal transducers through the rotor bore as described above until another anomaly indication is detected. The motor drive unit 30 continues to be stopped at each anomaly indication and awaits operator interaction until the predetermined test portion of the rotor specimen has been ultrasonically tested. The Scan program exits at point 224 and again returns the program execution to the executive at 212 awaiting further test information data from the test operator.

Hereabove, it has been described how the electronically controlled unit 38 adaptively controls and coordinates the operation of the motor drive unit 30 and the ultrasonic tester 44 in accordance with a function based on the detected anomaly indications within the rotor material of the test specimen. In accomplishing this the electronic control unit may be operative in a selected one of a plurality of control modes such as the SCAN mode, the MAX mode, and the STOP-ON-INDICATION mode. In either selected mode, the test data from the anomaly indications is recorded on the operator's console 52 and stored in the disc memory cartridges of the disc system 50 in formats which are desirable for analysis.

It is understood by anyone skilled in the microprocessor art that the invention need not be limited to any known family of microprocessor system components such as that shown in FIG. 5 pertaining to the Intel Corporation's System MDS-800, and that the operation of such an embodiment should not be limited to the particular detailed flow charts shown in FIGS. 6–11, but rather that applicant's invention should be construed in the breadth and broad scope of the appended claims here to follow.

I claim:

1. In a system for ultrasonically testing the material of a turbine rotor including at least one electronically controlled crystal transducer; a drive unit operative to axially insertably index said at least one crystal transducer within the bore of said turbine rotor under test in predetermined increments while arcuately rotating said at least one crystal transducer about the longitudinal axis of the rotor bore through a predetermined angle for each predetermined incremental index; and an electronic ultrasonic tester for activating said at least one crystal transducer at various indexed axial positions and angular orientations thereof within said rotor bore to transmit ultrasonic signals into said turbine rotor material and for receiving electrical signals from said at least one crysal transducer which are representative of back reflected echo signals corresponding to each transmitted ultrasonic signal, said ultrasonic tester being operative to generate measurable parameter test data signals including a first signal representative of the amplitude of the back reflected echo signal received from the at least one crystal transducer, a second signal which is representative of the depth location within the rotor material concurrently corresponding to an instantaneous amplitude value of said first signal, and at times, an anomaly indication which is representative of said first signal exceeding a preset reference threshold amplitude level, said anomaly indication representing the detection of a potential imperfection in said turbine rotor material, said drive unit being further operative to generate test data signals representative of measurable parameters including said axial position of the at least one crystal transducer within the rotor bore and the angular orientation thereof about the longitudinal axis of the rotor bore related to determining the location of a detected potential imperfection in said turbine rotor bore, the improvement comprising a programmed electronic controller including;

a memory unit for storing a plurality of programmed sets of instructions and data digital words which characterize the operation of said programmed electronic controller;

a microprocessor means operative to process said plurality of programmed sets of instructions and data digital words stored in said memory unit;

first means for electrically coupling said ultrasonic tester to said programmed electronic controller to coordinate the exchange of digital information therebetween in accordance with the processing operations of said microprocessor means, said first means being governed by said microprocessor means at predetermined times during the ultrasonic testing operation to observe said measurable parameter test data signals including said first and second signals and anomaly indications generated by said ultrasonic tester;

second means for electrically coupling said drive unit to said programmed electronic controller to coordinate the exchange of digital information therebetween in accordance with the processing operations of said microprocessor means, said second means being governed by said microprocessor means at predetermined times during the ultrasonic testing operations to observe said measurble test data signals including said axial position and angular orientations of said at least one crystal transducer generated by said drive unit and to adaptively control the drive unit in accordance with the values of the measured test data signals observed from said drive unit and ultrasonic tester and, at times, said generated anomaly indications; and an operator interactive device electrically coupled to said programmed electronic controller to coordinate the exchange of digital information therebetween in accordance with the processing operations of said microprocessor means, said operator interactive device being operative to enter instructional and initialization test information to said programmed electronic controller and to record ultrasonic test data resulting from the operation of the programmed electronic controller as governed by the microprocessor means included therein.

2. The programmed electronic controller in accordance with claim 1 wherein the drive unit is adaptively governed by the second means as directed by the microprocessor means in accordance with a selected one of a plurality of programmed control modes which include:

a first mode which directs the second means to govern the drive unit to continuously index the at least one crystal transducer through the rotor bore axially in the predetermined increments, the values of the test data signals observed by the first and second means corresponding to each generation and observation of an anomaly indication being stored in preassigned portions of the memory unit;

a second mode which directs the second means to govern the drive unit to index the at least one crystal transducer through the rotor bore axially in the predetermined increments and to cause the drive unit to stop at times under an anomaly indication is generated by the ultrasonic tester and observed by the first means, in each event the second means being thereafter directed to govern the drive unit to adjust the at least one crystal transducer about the axial position corresponding to the anomaly indication until the first signal is at a maximum amplitude, concurrently therewith the values of the signals which are observed by the first and second means respectively corresponding to each anomaly indication being stored in preassigned portions of the memory unit; and a third mode which directs the second means to govern the drive unit to index the at least one crystal transducer through the rotor bore axially in the predetermined increments and to cause the drive unit to stop at times when an anomaly indication is generated by the ultrasonic tester and observed by the first means, the values of the signals which are observed by the first and second means corresponding to the anomaly indication being stored in preassigned portions of the memory unit, the second means being responsive to further govern the drive unit, after an anomaly indication, only upon an operator restart request.

3. The programmed electronic controller in accordance with claim 2 wherein the depth value of each anomaly indication stored in the preassigned portion of the memory unit is corrected in accordance with a function based on the angle of the plane in which the at least one crystal transducer is disposed within the rotor bore with respect to the plane which is perpendicular to the longitudinal axis of the rotor bore to provide an effective depth value for each anomaly indication; and wherein an effective anomaly area is derived by a function based on a known calibration area value and a constant value derived from a percent of full scale amplitude signal corresponding to the anomaly.

4. The programmed electronic controller in accordance with claim 3 wherein the ultrasonic test data are recorded on the operator interactive device in sequential order respectively corresponding to the occurrences of the anomaly indications as the at least one crystal transducer is axially positioned through the turbine rotor bore; and wherein each test data recordation comprises: the anomaly indication sequential number, the related axial position at angular orientations of the crystal transducer concurrent with the detection of the anomaly indication, the effective depth value, anomaly signal amplitude and the derived effective area of the anomaly within the rotor material.

5. The programmed electronic controller in accordance with claim 1 wherein the ultrasonic tester includes a receiver amplifier for amplifying the electrical signals received from the at least one crystal transducer, the gain of said receiver amplifier being characterized as a function of depth location within the rotor material, whereby the receiver amplifier amplifies the received electrical signal with a gain level corresponding to the depth location in the rotor material from where it is being back reflected, said amplified electrical signal being normalized to a predetermined signal level range; and wherein said normalized amplified electrical signal is the first signal generated by the ultrasonic tester and observed by the first means.

6. The programmed electronic controller in accordance with claim 5 wherein said first means is governed by said microprocessor means, at times when it is determined that the amplitude of the observed first signal is greater than its normalized predetermined signal level range, to adjust the gain characteristics of the receiver amplifier of the ultrasonic tester to bring the amplitude of the observed first signal back within the normalized predetermined signal level range.

7. The programmed electronic controller in accordance with claim 1 and additionally operative in accordance with the processing operations of the microprocessor means to uncover within the turbine rotor material an axial dimension interval, associated with a common angular interval of crystal transducer rotation, over which the number of generated anomaly indications observed by the first means exceeds a preset number, said first means being directed, thereupon, to govern the drive unit to reposition the at least one crystal transducer to an axial position within the rotor base corresponding to the approximate beginning of said uncovered axial dimension interval and thereafter, to proceed with the forward axial indexing with a smaller predetermined indexing increment, whereby a closer inspection of the turbine rotor material volume corresponding to the uncovered axial dimension interval and the common angular interval is accomplished.

8. The programmed electronic controller in accordance with claim 7 wherein the axial indexing of the at least one crystal transducer at the smaller predetermined increments for closer inspection of the turbine rotor material volume is terminated after the uncovered axial dimension interval has been traversed by the at least one crystal transducer.

9. The programmed electronic controller in accordance with claim 7 wherein the predetermined axial indexing increment is one-fourth inch and the smaller predetermined axial indexing increment is one-eighth inch.

* * * * *